United States Patent [19]
Lodewijk et al.

[11] Patent Number: 5,565,565
[45] Date of Patent: Oct. 15, 1996

[54] PREPARATION OF N-9 SUBSTITUTED GUANINE COMPOUNDS

[75] Inventors: Eric Lodewijk, Boulder; Yeun-Kwei Han, Louisville; George C. Schloemer, Longmont; Sam L. Nguyen, Denver, all of Colo.

[73] Assignee: Syntex (U.S.A.) Inc., Palo Alto, Calif.

[21] Appl. No.: 286,045

[22] Filed: Aug. 4, 1994

[51] Int. Cl.$^6$ .................................................. C07D 473/18
[52] U.S. Cl. .................................................. 544/276
[58] Field of Search ................................. 544/276

[56] References Cited

U.S. PATENT DOCUMENTS

| | | | |
|---|---|---|---|
| 4,355,032 | 10/1982 | Verheyden et al. | 424/253 |
| 4,360,522 | 11/1982 | Schaeffer et al. | 424/253 |
| 4,621,140 | 11/1986 | Verheyden et al. | 544/276 |
| 5,250,535 | 10/1993 | Verheyden et al. | 514/262 |

FOREIGN PATENT DOCUMENTS

| | | |
|---|---|---|
| 602464 | 3/1987 | Australia . |
| 072027 | 2/1983 | European Pat. Off. . |
| 0074306 | 3/1983 | European Pat. Off. . |
| 152965 | 8/1985 | European Pat. Off. . |
| 0260596 | 3/1988 | European Pat. Off. . |
| 0400686 | 12/1990 | European Pat. Off. . |
| 532878 | 3/1993 | European Pat. Off. . |
| 05213903 | 9/1991 | Japan . |
| 2047457 | 2/1994 | Spain . |

OTHER PUBLICATIONS

Vorbruggera, tet. Letters 1978 1339.
Vorbrugger Chem. Ber 114, 1234 (1981).
Kim I, Bull. Korean Chem Soc. 9, 295 (1988).
Kim II, Heterocycles 27, 71 (1988).
Kim III Chemistry Letters 1988, 1045.
Robbins, Nucleosides & Nucleo tides 8, 725–741 (1989).
J. Kjellberg et al., *Nucleosides Nucleotides*, 8(2), pp. 225–256 (1989).
Zhongguo Yaoke Daxue Xuebao, 23(1), pp. 43–44 (1992).
F. P. Clausen et al., *Org. Prep. Proced. Int*, 25(4), pp. 375–401 (1993).
H. Matsumoto et al., *Chem. Pharm. Bull.*, 36(3), 1153–1157 (1988).
D. P. C. McGee et al., *Synthetic Communications*, 18(14), 1651–1660 (1988).
J. C. Martin et al., *J. Med. Chem.*, 26, 759–761 (1983).
"Production of 9-[2-Hydroxyethoxy)methyl]-guanine", *Patent Abstracts of Japan*, 12: 353 (C–530) [3200] (1988) [abstract of Japanese Patent Kokai No. 107982/1988 (May 1988)].

*Primary Examiner*—Mark L. Berch
*Attorney, Agent, or Firm*—Heller Ehrman White & McAuliffe

[57] ABSTRACT

The invention relates to efficient and selective processes for the synthesis of the antiviral N-9 substituted guanine compounds acyclovir and ganciclovir.

24 Claims, No Drawings

PREPARATION OF N-9 SUBSTITUTED GUANINE COMPOUNDS

BACKGROUND OF THE INVENTION

1. Field of the Invention

The present invention relates to processes for the synthesis of antiviral N-9 substituted guanine compounds.

2. Background Information and Related Disclosures

Many synthetic N-substituted derivatives of purines and related nucleosides have been shown to exhibit significant antiviral properties. Most notable are the N-9 alkylated products 9-[(1,3-dihydroxy-2-propoxy)methyl]guanine (i.e. ganciclovir) and 9-[(2-hydroxyethoxy)methyl]guanine, (i.e. acyclovir). It is clearly desirable to have inexpensive and efficient processes for manufacturing these and similar compounds.

The usefulness of any process for manufacturing chemical compounds is gauged by several factors. For example, starting materials should be as simple structurally as feasible (so as to keep their costs low). The process is more efficient if intermediates do not require isolation and/or purification, since these procedures result in additional steps and lower yield. The process should yield a product that is free of by-products (e.g., undesired isomers, side-products and reagents). Shortcomings in any of the above parameters result in increased manufacturing costs, which impacts negatively on the desirability of the process.

The simplest synthetic approach to the N-9 substituted guanine compounds involves the direct alkylation of a protected guanine base. However, there are significant drawbacks to this approach. In many reported processes, guanine protected by acyl groups (for example, diacetylguanine) is employed as the protected guanine base. However, acyl groups may prove difficult to remove at the completion of the process, resulting in lower yields. Also, known alkylation processes are not regiospecific for the N-9 position of the protected guanine base, and result in a mixture of N-9 and N-7 alkylation products. The unwanted N-7 isomer is difficult to separate from the desired N-9 compound, requiring chromatography for isolation. Chromatographic separation on a commercial scale is most undesirable, because of the increased costs associated with such a separation (cost of solvents and stationary phase, low yields of desired product, etc).

Surprisingly, efficient and selective processes for preparing N-9 substituted guanine compounds, including ganciclovir and acyclovir, have been discovered. The processes are essentially specific for the preparation of the N-9 isomer, since the alkylation step provides a high N-9/N-7 ratio of alkylated guanine product (a ratio of greater than 30:1 may be achieved), thus eliminating the need for the chromatographic separation of the N-9/N-7 isomer mixture. The processes also provide high yields, require simple starting materials and reaction conditions, and are carried out from start to finish in a single reaction vessel, delivering acyclovir and ganciclovir in greater than 99% purity.

Previous processes for the preparation of acyclovir and similar compounds are disclosed in U.S. Pat. Nos. 4,355,032, 4,360,522, 4,621,140, and 5,250,535, European Patent Applications 152,965, 532878, and 72027, and JP 5213903. Syntheses of related compounds are disclosed in *Nucleosides Nucleotides*, 8 (2), pp 225–256 (1989), *Zhongguo Yaoke Daxue Xuebao*, 23 (1), pp 43–44 (1992), *Org. Prep. Proced. Int*, 25(4), pp 375–401 (1993), *J. Med. Chem.*, 26(5), 759–61 (1983), *Synth. Commun.*, 18(14), 1651–60 (1988), and *Chem. Pharm. Bull.*, 36 (3), 1153–1157 (1988)

SUMMARY OF THE INVENTION

One aspect of the invention relates to an efficient and selective process for the preparation of an alkylated guanine compound of the formula:

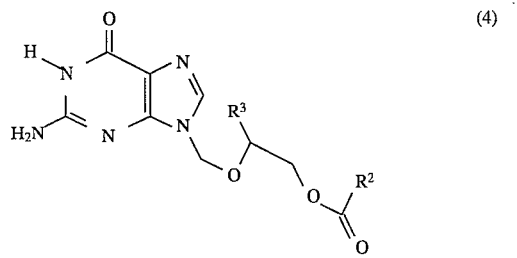

wherein:

$R^2$ is lower alkyl; and $R^3$ is hydrogen or —$CH_2OC(O)R^4$;

in which $R^4$ is lower alkyl;

said process comprising:

contacting a compound or mixture of compounds represented by the formula:

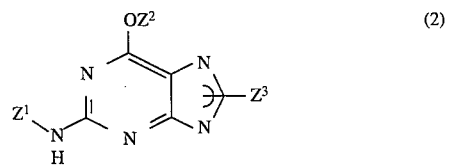

wherein:

$Z^1$ is hydrogen or $R^5R^6R^7Si$;

$Z^2$ is hydrogen or $R^5R^6R^7Si$;

$Z^3$ is hydrogen or $R^5R^6R^7Si$;

in which $R^5$, $R^6$, and $R^7$ are independently lower alkyl; provided that at least one of $Z^1$, $Z^2$, and $Z^3$ is $R^5R^6R^7Si$; with a compound of the formula:

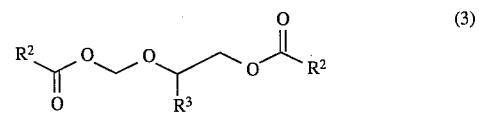

where $R^2$ and $R^3$ are as defined above; in the presence of a selective alkylation catalyst.

The invention also relates to an efficient and selective process for preparing compounds represented by the formula:

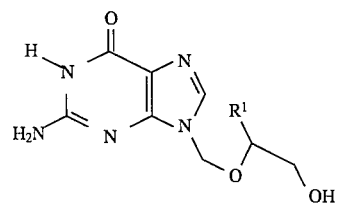

wherein:

$R^1$ is hydrogen or —$CH_2OH$; said process comprising:

a) contacting a compound represented by the formula:

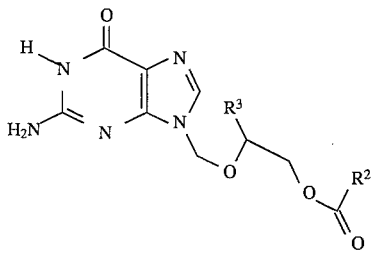
(4)

where $R^2$ and $R^3$ are as defined above: with an acylating agent having an acyl radical of formula $R^8C(O)$—, where $R^8$ is lower alkyl;
optionally in the presence of an organic base, to give a compound represented by the formula:

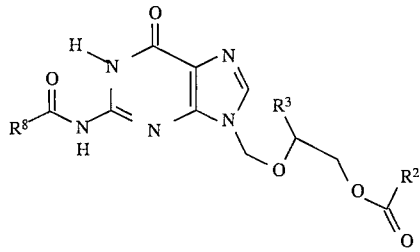
(6)

where $R^2$, $R^3$ and $R^8$ are as defined above;
c) separating the compound of Formula (6); and
d) hydrolyzing the separated compound of Formula (6).
Alternatively, a process for preparing compounds represented by the formula:

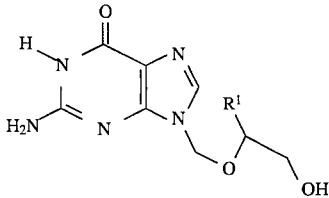

wherein:
$R^1$ is hydrogen or —CH$_2$OH; comprises:
a) contacting a mixture of isomers represented by the formula:

(2a)

where $R^5$, $R^6$, and $R^7$ are as defined above and $R^8$ is lower alkyl or optionally substituted phenyl;
with a compound represented by the formula:

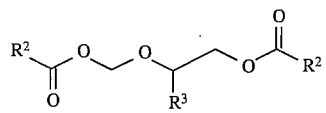
(3)

wherein:
$R^2$ is lower alkyl; and
$R^3$ is hydrogen or —CH$_2$OC(O)R$^4$;
in which $R^4$ is lower alkyl;
in the presence of a selective alkylation catalyst, to give a compound represented by the formula:

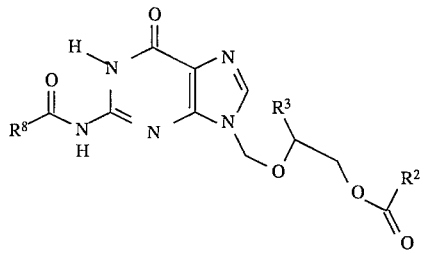
(6)

where $R^2$, $R^3$ and $R^8$ are as defined above;
c) separating the compound of Formula (6); and
d) hydrolyzing the separated compound of Formula (6).

DETAILED DESCRIPTION OF THE INVENTION

DEFINITIONS AND GENERAL PARAMETERS

The following definitions are set forth to illustrate and define the meaning and scope of the various terms used to describe the invention herein.

The term "alkyl" means a monoradical branched or unbranched saturated hydrocarbon chain containing 1 to 12 carbon atoms, such as methyl, ethyl, propyl, tert-butyl, n-hexyl, n-octyl, n-decyl, unless otherwise indicated.

The term "lower alkyl" means a monoradical branched or unbranched saturated hydrocarbon chain containing 1 to 6 carbon atoms, such as methyl, ethyl, n-propyl, isopropyl, n-butyl, tert-butyl, n-pentyl, n-hexyl, unless otherwise indicated.

The term "acylating agent" refers to either an anhydride or an acyl halide.

The term "anhydride" refers to compounds of the general structure RC(O)—O—C(O)R where R is lower alkyl or optionally substituted phenyl (e.g., acetic anhydride where R is methyl, propionic anhydride where R is ethyl, benzoic anhydride where R is phenyl).

The term "acyl halide" refers to the group RC(O)X, where R is lower alkyl or optionally substituted phenyl and X is bromo or chloro (e.g., acetyl bromide where R is methyl and X is bromo, propionyl chloride where R is ethyl and X is chloride, benzoyl chloride where R is phenyl and X is chloro).

Thus the term "acylating agent having an acyl radical of formula $R^8C(O)$—" refers to an anhydride of formula $R^8C(O)OC(O)R^8$, or an acyl halide of formula $R^8C(O)X$, where $R^8$ is lower alkyl or optionally substituted phenyl and X is bromo or chloro.

The term "base" includes both strong bases and organic bases. The term "strong base" refers to bases such as sodium hydroxide, potassium hydroxide, lithium hydroxide, ammonium hydroxide, sodium bicarbonate, potassium carbonate.

The term "organic base" refers to bases such as triethylamine, 4-pyrrolidinopyridine, dimethylaminopyridine (DMAP), N-methylmorpholine, N-ethylmorpholine, pyridine, dialkylanilines, diisopropylcyclohexylamine.

The term "silylation catalyst" as used herein refers to catalysts that promote the silylation of guanine, for example ammonium sulfate, p-toluenesulfonic acid, trifluoromethane sulfonic acid, trimethylsilyl trifluoromethanesulfonate, bistrimethylsilyl sulfonate, sulfuric acid, potassium butylsulfonate, ammonium perchlorate, sodium perchlorate, sodium borofluoride, tin tetrachloride.

The term "selective alkylation catalyst" as used herein refers to catalysts that promote the regiospecific alkylation of guanine or protected guanine at the N-9 position, for example trimethylsilyl perchlorate, trifluoromethane sulfonic acid, trimethylsilyl trifluoromethanesulfonate, and bistrimethylsilyl sulfonate.

The terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

The term "hydrolyzing" or "hydrolysis" refers to the process of splitting a chemical bond by the addition of water; for example, hydrolysis of an alkyl ester gives an organic acid and an alcohol, hydrolysis of an amide gives an organic acid and an amine, hydrolysis of a silyl ether gives an alcohol. Hydrolysis may be accomplished by treatment with an inorganic acid, for example sulfuric acid, hydrochloric acid, hydrobromic acid, and the like, or by treatment with a strong base as defined above.

"Optional" or "optionally" means that the subsequently described event or circumstance may or may not occur, and that the description includes instances where said event or circumstance occurs and instances in which it does not. For example, "optionally in the presence of an organic base" with reference to a chemical reaction means that an organic base may or may not be present in the reaction in order for the reaction to proceed.

The term "silylating agent" as used herein refers to a compound capable of silylating guanine. A preferred silylating agent is hexamethyldisilazane (which will give a compound of Formula (2) in which $R^5$, $R^6$, and $R^7$ are all methyl). However, many other silylating agents are known in the art. For example, guanine may be reacted with a trialkylsilyl halide of formula $SiR^5R^6R^7X$, in which $R^5$, $R^6$, and $R^7$ are independently lower alkyl and X is chloro or bromo, such as trimethylsilyl chloride, tert-butyldimethylsilyl chloride, and the like, preferably in the presence of about 1–2 molar equivalents of a base.

The compound of Formula (2) is represented as follows:

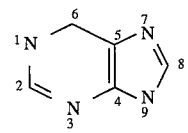

(2)

Formula (2) represents guanine protected by one, two, or three silyl groups, or a mixture thereof, where $Z^1$, $Z^2$, and $Z^3$ are independently hydrogen or a silyl group of formula $SiR^5R^6R^7$, provided that at least one of $Z^1$, $Z^2$, and $Z^3$ must be a silyl group, in which $R^5$, $R^6$, and $R^7$ are independently lower alkyl. It should be noted that Formula (2) as drawn represents a mixture of N-7 and N-9 isomers (as a tautomeric mixture).

Isolation and purification of the compounds and intermediates described herein can be effected, if desired, by any suitable separation or purification procedure such as, for example, filtration, extraction, crystallization, column chromatography, preparative high pressure liquid chromatography (preparative HPLC), thin-layer chromatography or thick-layer chromatography, or a combination of these procedures. Specific illustrations of suitable separation and isolation procedures can be had by reference to the examples hereinbelow. However, other equivalent separation or isolation procedures can also be used.

Nomenclature

The following numbering and nomenclature system will be used for describing and naming the compounds of the invention.

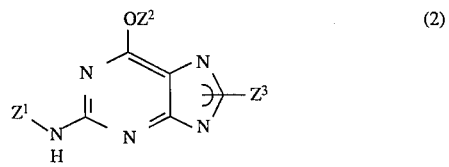

Some representative compounds are named in the following examples.

The compound of Formula I where $R^1$ is hydrogen is named 9-(2-hydroxyethoxymethyl)guanine, i.e., acyclovir.

The compound of Formula I where $R^1$ is —CH$_2$OH is named 9-(1,3-dihydroxy- 2-propoxymethyl)guanine, i.e., ganciclovir.

SUMMARY OF THE PROCESS FOR PREPARING COMPOUNDS OF FORMULA I

The compounds of Formula I are synthesized as described with reference to Reaction Scheme A.

REACTION SCHEME A

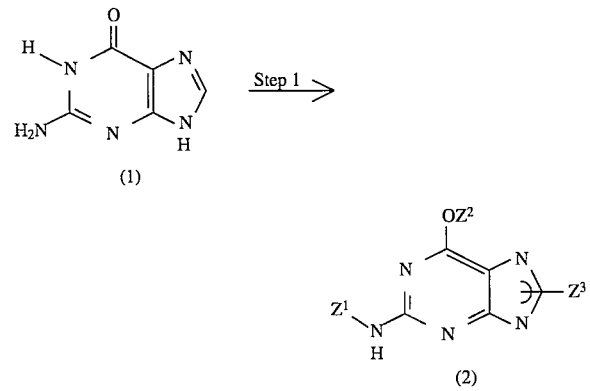

where $Z^1$, $Z^2$ and $Z^3$ are independently hydrogen or a silyl protecting group of the formula $R^5R^6R^7Si$, in which $R^5$, $R^6$, and $R^7$ are independently lower alkyl, provided that at least one of $Z^1$, $Z^2$ and $Z^3$ is a silyl group;

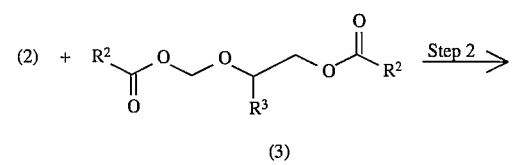

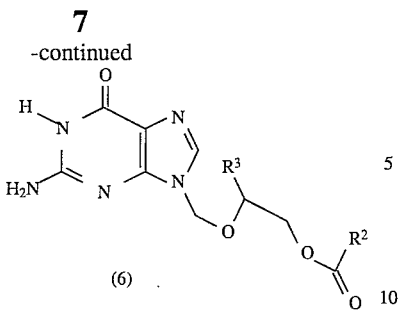

(6)

where $R^2$ is lower alkyl, and $R^3$ is hydrogen or —$CH_2OC(O)R^4$, in which $R^4$ is lower alkyl;

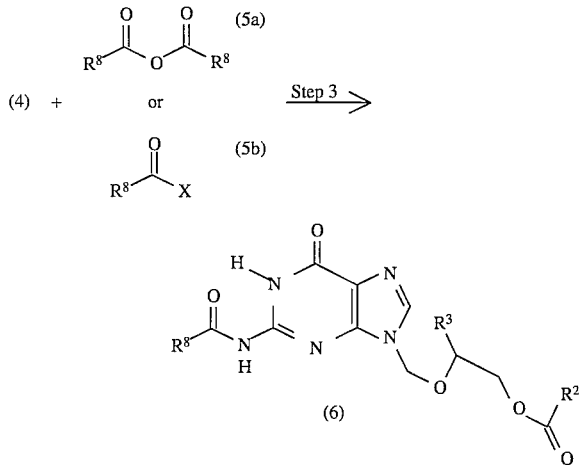

where $R^8$ is lower alkyl or optionally substituted phenyl and X is chloro or bromo;

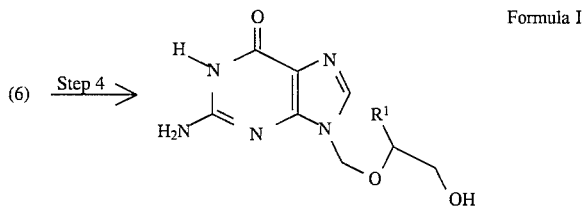

Formula I where $R^2$ is lower alkyl and M is an alkali metal.

Step 1: Preparation of Formula (c)

As illustrated in Reaction Scheme B, Step 1, 1,3-dichloro-2-propanol (Formula (a)) is reacted with paraformaldehyde (b) and hydrochloric acid to give the corresponding compound of Formula (c).

A mixture of 1,3-dichloro-2-propanol, paraformaldehyde (about 1 to 2 molar equivalents, preferably about 1.5 molar equivalents), in an inert solvent, preferably methylene chloride, is reacted at a temperature of about −10° to 5° C., preferably about −5° C., with hydrogen chloride gas, over a period of about 10 minutes to 1 hour, preferably about 25 minutes. When the reaction is substantially complete, 2-(chloromethoxy)-1,3-dichloropropane, the compound of Formula (c), is isolated by conventional means.

Step 2: Preparation of Formula (3a)

As illustrated in Reaction Scheme B, Step 2, 2-(chloromethoxy)-1,3dichloropropane (Formula (c)) is reacted with a compound of the formula $R^2C(O)OM$ to give the corresponding compound of Formula (3).

A mixture of a compound of the formula $R^2C(O)OM$, preferably where $R^2$ is ethyl and M is sodium or potassium, most preferably sodium (about 2 to 7 molar equivalents, preferably about 3.5 molar equivalents) in an inert solvent, preferably toluene, is reacted with 2-(chloromethoxy)-1,3-dichloropropane at about reflux temperature, to give 1,3-dichloro-2-propyloxymethyl propionate as an intermediate. To this refluxing mixture is added tetrabutylphosphonium chloride (about 0.05 to 0.3 molar equivalents, preferably about 0.1 molar equivalents) in an inert solvent, preferably toluene, and reflux is continued over a period of 4 to 24 hours, preferably about 12 hours. When the reaction is substantially complete, the compound of Formula (3a) is isolated by conventional means.

Reaction Scheme A

Step 1: Preparation of Formula (2)

As illustrated in Reaction Scheme A, Step 1, guanine (Formula (1)) is silylated to give the corresponding protected compound of Formula (2).

The protection of guanine prior to alkylation is well known in the art (see, for example "Synthesis of 9-substituted Guanines. A Review" by F. P. Clausen and J. J. Christensen *Org. Prep. Proced. Int*, 25(4), pp 375–401 (1993)). Guanine may be, for example, be protected using acyl groups, for example acetyl, or by silyl groups. Traditionally, when silyl groups are employed for protection,

Starting Materials

The trialkylsilyl halides of formula $R^5R^6R^7SiX$ (where X is chloro or bromo) or hexamethyldisilazane are commercially available. Compounds of Formula (3) where $R^3$ is hydrogen are prepared by means well known in the art, for example by reaction of 1,3-dioxolane and acetic anhydride. Compounds of Formula (3) where $R^3$ is $CH_2C(O)R^4$, shown below as a compound of Formula (3a) where $R^2$ and $R^4$ are the same and are lower alkyl, may be prepared as shown in Reaction Scheme B below:

REACTION SCHEME B

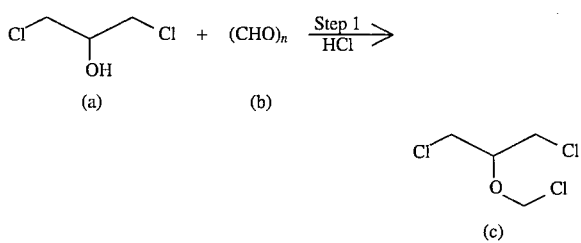

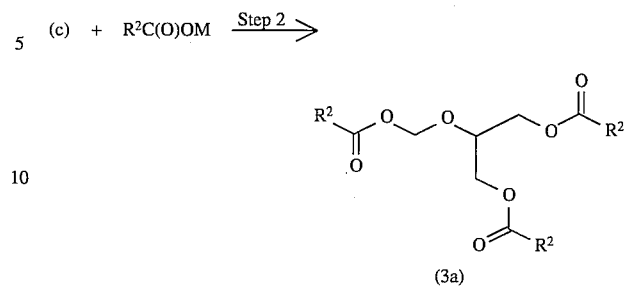

guanine is silylated in such a manner that all active protons present in guanine are replaced by a silyl group before proceeding with the desired reaction, i.e. guanine is protected as the trisilyl derivative. However, it has now been discovered that, although trisilylation of guanine followed by the alkylation of Step 2 gives the desired product in good yield, and indeed is preferred, it is not essential that guanine be trisilylated for the alkylation carried out in Step 2 to be essentially specific for the preparation of the N-9 isomer. Conventionally, guanine as a slurry is reacted with a silylating agent, for example hexamethyldisilazane, at reflux until all suspended material goes into solution, which signals the complete formation of the trisilyl derivative. This reaction can take up to 48 hours or more. Surprisingly, it has now been found that refluxing for much less time, for example as little as 2 hours, then reacting the slurry thus produced with a compound of Formula (3) as described in Step 2 below, gives good yields of desired product. This result is clearly advantageous, since less expense is involved in a shortened reaction time, and smaller amounts of silylating reagent are used. Although the composition of a compound of Formula (2) produced by reacting guanine with hexamethyldisilazane for a shortened period of time is not yet known with any certainty, it is believed to be mainly a monosilyl derivative, probably mixed with some disilyl and trisilyl guanine.

In one preferred method, guanine is reacted with about 3–10 molar equivalents of a silylating agent, preferably with hexamethyldisilazane (i.e. to give a compound of Formula (2) where $R^5$, $R^6$, and $R^7$ are all methyl), in the presence of an silylation catalyst, preferably ammonium sulfate, trifluoromethanesulfonic acid, trimethylsilyltrifluoromethane sulfonate, or bistrimethylsilyl sulfonate, most preferably trifluoromethanesulfonic acid (about 0.01 to 0.1 molar equivalents). The mixture is heated to reflux over a period of about 5–24 hours, preferably about 16 hours. When the reaction is substantially complete, excess silylating agent is removed under reduced pressure, and the resultant solution of the protected guanine product of Formula (2) is used in the next step without further purification.

Alternatively, guanine is reacted with a silylating agent, preferably hexamethyldisilazane, in the presence of a silylating catalyst, preferably trifluoromethanesulfonic acid, as described in the preceding paragraph, but for a period of about 1–8 hours, preferably 2–4 hours. Optionally, excess silylating agent is removed under reduced pressure, and the resultant mixture of the protected guanine product of Formula (2) is used in the next step without further purification.

Alternatively, guanine may be reacted with 1–5 molar equivalents of a trialkylsilyl halide of formula $SiR^5R^6R^7X$, in which $R^5$, $R^6$, and $R^7$ are independently lower alkyl and X is chloro or bromo, such as trimethylsilyl chloride, tert-butyldimethylsilyl chloride, and the like, in the presence of about 1–5 molar equivalents of a base.

It should be noted that ammonium sulfate, trifluoromethanesulfonic acid, trimethylsilyltrifluoromethane sulfonate, or bistrimethylsilyl sulfonate work well as silylation catalysts in the silylation of guanine described above. However, use of trifluoromethanesulfonic acid is preferred because it is much less expensive than trimethylsilyltrifluoromethane sulfonate or bistrimethylsilyl sulfonate, and is particularly preferred because trifluoromethanesulfonic acid is converted to trimethylsilyltrifluoromethane sulfonate during the course of the silylation reaction, which then functions as the preferred selective alkylation catalyst in Step 2 (i.e. no further catalyst need be added for Step 2).

Step 2: Preparation of Formula (4)

As illustrated in Reaction Scheme A, Step 2, protected guanine (Formula (2)) is selectively alkylated to give the corresponding N-9 isomer of Formula (4), plus a small amount of the N-7 isomer.

The solution or slurry obtained from Step 1 is heated to a temperature in the range of about 75°–115° C., preferably about 100° C. To the solution is added a compound of Formula (3) where $R^2$ is lower alkyl, and $R^3$ is hydrogen or $—CH_2OC(O)R^4$, where $R^4$ is lower alkyl, and a selective alkylation catalyst (about 0.01 to 0.1 molar equivalents), such as trifluoromethanesulfonic acid, trimethylsilyltrifluoromethane sulfonate, or bistrimethylsilyl sulfonate, and the like, preferably trimethylsilyltrifluoromethane sulfonate. As noted above, if trifluoromethanesulfonic acid was employed as the catalyst in Step 1, then the preferred trimethylsilyltrifluoromethane sulfonate is formed in situ, and the addition of further selective alkylation catalyst is not necessary.

The reaction mixture is heated to a temperature in the range of about 110° C. to 140° C., preferably about 120° C., for a period of about 1.5 to 12 hours, preferably about 8 hours. Preferably, excess compound of Formula (3) is removed under reduced pressure, yielding a solution of the desired compound of Formula (4), along with a small amount of the undesired N-7 isomer.

Step 3: Preparation of Formula (6)

As illustrated in Reaction Scheme A, Step 3, the N-9 isomer of Formula (4) is acylated and recrystallized, thus removing any residue of the N-7 isomer, to give the pure compound of Formula (6).

The solution from Step 2 is heated to a temperature in the range of about 75°–140° C., preferably about 100° C. To the solution is added a mixture of an organic base, such as triethylamine, pyridine, and the like, preferably 4-dimethylaminopyridine (about 0.05 to 0.1 molar equivalents), and an anhydride of formula $R^8C(O)OC(O)R^8$ (5a) or acyl halide of formula $R^8C(O)X$ (5b), in which $R^8$ is lower alkyl or optionally substituted phenyl and X is chloro or bromo. If an acyl halide is used, a further 1–2 molar equivalents of a base are also added. Preferably an anhydride where $R^8$ is ethyl (about 1.2 to 3 molar equivalents) is employed. The mixture is heated to a temperature in the range of about 90° to 130° C., preferably about 100° C., for a period of about 0.5 to 2 hours, preferably about 1 hour. The reaction mixture is cooled to about room temperature, and unreacted acylating agent quenched by the addition of methanol and an inert solvent, preferably toluene. The reaction mixture is refluxed for about 1 hour, and then slowly cooled to −10° to 20° C., preferably about 0° C., and stood for 30 minutes to 6 hours, preferably about 1 hour. Pure compound of Formula (6) is obtained as a crystalline solid, with the N-7 isomer remaining in solution.

Step 4: Preparation of Formula I

As illustrated in Reaction Scheme A, Step 4, the pure compound of Formula (6) is hydrolyzed to give the corresponding compound of Formula I.

The acylated guanine compound of Formula (6) is dissolved in a mixture of a protic solvent (about 15–30 molar equivalents), preferably methanol, and a strong base (about 5–20 molar equivalents), preferably ammonium hydroxide, at a temperature in the range of about 40° to 60° C., preferably about 50° C., at a pressure of about 10 psi, for a period of about 6 to 24 hours, preferably about 16 hours. The methanol and ammonium hydroxide is removed by distillation, and methanol (about 15–30 molar equivalents) is added back to the reaction mixture, which is then heated to reflux for about 1 hour. The reaction mixture is cooled to about 0° C. for a period of about 1 hour, filtered and washed with methanol. The solid is optionally recrystallized, preferably from water, yielding the desired 9-substituted guanine compound of Formula I.

Alternative Process for the Preparation of Compounds of Formula I

The compounds of Formula I may also be synthesized as described in Reaction Scheme C.

REACTION SCHEME C

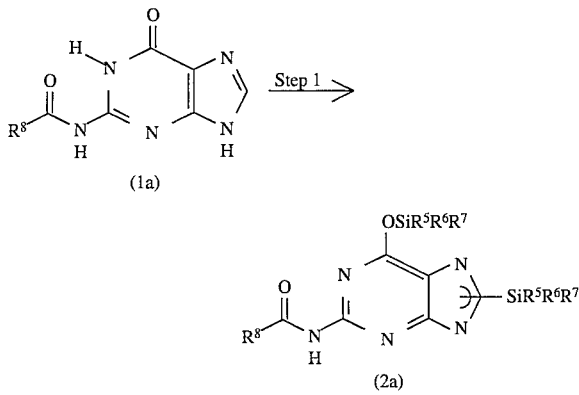

where $R^8$ is lower alkyl or optionally substituted phenyl, and $R^5$, $R^6$, and $R^7$ are independently lower alkyl;

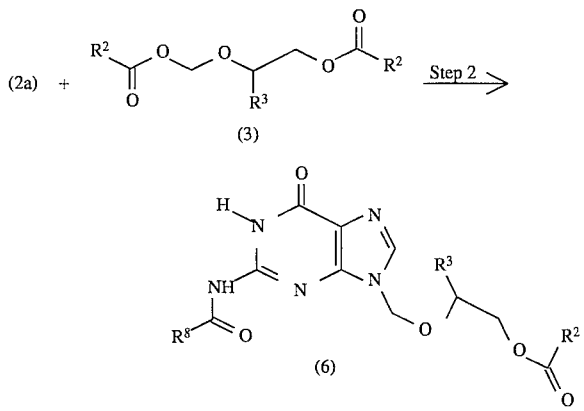

where $R^2$ is lower alkyl, and $R^3$ is hydrogen or —$CH_2OC(O)R^4$, in which $R^4$ is lower alkyl;

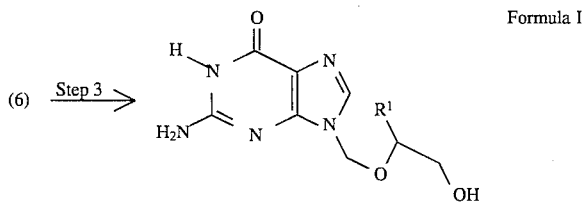

where $R^1$ is hydrogen or —$CH_2OH$.

Starting Materials

The N-2 acylguanines of Formula (1a) are commercially available, for example from Aldrich.

Step 1: Preparation of Formula (2a)

As illustrated in Reaction Scheme C, Step 1, 2-acylguanine (Formula (1a)) is silylated to give the corresponding protected compound of Formula (2a). The reaction is carried out as shown for the preparation of compounds of Formula (2), in Reaction Scheme A, Step 1.

Step 2: Preparation of Formula (6)

As illustrated in Reaction Scheme C, Step 2, protected N-2 acylguanine (Formula (2a)) is selectively alkylated to give the corresponding N-9 isomer of Formula (6), plus a small amount of the N-7 isomer. The reaction is carried out as shown for the preparation of compounds of Formula (4), in Reaction Scheme A, Step 2.

Step 3: Preparation of Formula I

As illustrated in Reaction Scheme C, Step 3, the pure compound of Formula (6) is hydrolyzed to give the corresponding compound of Formula I. The reaction is carried out as shown for the preparation of compounds of Formula I, in Reaction Scheme A, Step 4.

PREFERRED PROCESSES AND LAST STEPS

A preferred process for synthesis of N-9 substituted guanine compounds entails first protecting guanine with trialkylsilyl, preferably trimethylsilyl, most preferably as tris(trimethylsilyl), reacting this protected compound with a compound of formula $R^2C(O)OCH_2OCH(R^3)CH_2OC(O)R^2$, preferably where $R^2$ is ethyl and $R^3$ is —$CH_2OC(O)C_2H_5$, to give an N-9 substituted guanine along with a small amount of the N-7 isomer. This compound is then acylated with an acylating agent of formula $R^8C(O)OC(O)R^8$ or $R^8C(O)X$, where $R^8$ is preferably ethyl, and crystallized to give pure N-2-acyl N-9 substituted guanine, which is hydrolysed to give the desired N-9 substituted guanine.

A second preferred process involves first protecting N-2 acylguanine with trialkylsilyl, preferably trimethylsilyl, reacting this protected compound with a compound of formula $R^2C(O)OCH_2OCH(R^3)CH_2OC(O)R^2$, preferably where $R^2$ is ethyl and $R^3$ is —$CH_2OC(O)C_2H_5$, to give an N-9 substituted guanine along with a small amount of the N-7 isomer. This compound is then crystallized to give pure N-2-acyl N-9 substituted guanine, which is hydrolysed to give the desired N-9 substituted guanine.

EXAMPLES

The following preparations and examples are given to enable those skilled in the art to more clearly understand and to practice the present invention. They should not be considered as limiting the scope of the invention, but merely as being illustrative and representative thereof.

Example 1

Preparation of Compounds of Formula (I) where $R^1$ is —$CH_2OH$

1A. Formula (4) where $R^2$ is Ethyl and $R^3$ is —$C_2OC(O)CH_2CH_3$

A mixture of guanine (10 g), hexamethyldisilazane (HMDS, 50 ml), and trifluoromethane sulfonic acid (0.24 ml) was heated to reflux (130°–135° C.) for 16 hours. The resulting mixture was cooled to 35° C., and excess HMDS removed by distillation (0.1 to 1 mm Hg), slowly raising the bath temperature back to 105° C. The mixture was then cooled to 100° C., and 3-propionyloxy-2-propionyloxymethoxypropyl propionate (23.04 g) added. The resulting mixture was heated to 120°–125° C. for 8 hours, and the low boiling material removed by distillation. The resulting reaction mixture, persilyl 9-(1,3-dipropionoxy- 2-propoxymethyl)guanine as a solution, was cooled to 100° C. and used as such in the next reaction without further purification. The N-9 to N-7 alkylation ratio obtained in this reaction was typically between about 20:1 to 30:1.

1B. Formula (6) where $R^2$ is Ethyl, $R^3$ is —$CH_2OC(O)CH_2CH_3$, and $R^8$ is Ethyl To the resulting reaction mixture of Example 1A at 100° C. was added a mixture of dimethylaminopyridine (0.663 g) and propionic anhydride (12.8 ml), and the mixture was stirred at 100° C. for 1 hour. A mixture of methanol (3.95 ml) and toluene (100 ml) was then added, and the mixture refluxed for 30 minutes. The resulting solution was slowly cooled to 0° C. over 2 hours, and maintained at 0° C. for 1 hour. The precipitate thus obtained was filtered off, washed with toluene (50–100 ml), and dried under reduced pressure (45° C., 60 mm) to afford 9-(1,3-propionoxy-2-propoxymethyl)-$N^2$-propionylguanine (21 g).

Similarly, by following the procedures described above in Example 1B and substituting propionic anhydride with other compounds of Formula (5a) or (5b), the following compounds of Formula (6) are prepared:

9-(1,3-dipropionoxy-2-propoxymethyl)-$N^2$-acetylguanine;

9-(1,3-dipropionoxy-2-propoxymethyl)-$N^2$-butyrylguanine; and 9-(1,3-dipropionoxy-2-propoxymethyl)-$N^2$-benzoylguanine.

1C. Preparation of Formula I Where $R^1$ is —$CH_2OH$ 9-(1,3-propionoxy-2-propoxymethyl)-$N^2$-propionylguanine (10 g) was mixed with methanol (15 ml) and ammonium hydroxide (12 ml of 28%) at 53° C. under 10.5 psi pressure for 16 hours. Methanol and aqueous ammonium hydroxide were removed by distillation under reduced pressure, and methanol (50 ml) was added to the residue. The mixture was refluxed for 1 hour, cooled to 0° C., and methanol removed by decantation. To the remaining crude product was added hot water (150 ml at 92°–95° C.), along with PWA Carbon (0.3 g) and Celatom (0.15 g). The mixture was stirred and filtered hot, and the cake washed with water (2×10 ml at 90°–95° C.). The filtrate was cooled to 0° C. and the crystalline product filtered off, to give pure 9-(1,3-dihydroxy-2-propoxymethyl)guanine (5.4 g). Characteristic analytical data are as follows: $^1$H-NMR (DMSO-$d_6$), δ10.58 (1H, s, —NHCO), 7.78 (1H, s, N=CH—N), 6.46 (2H, br s, —$NH_2$), 5.42 (2H, s, N—$CH_2$—O), 4.58 (2H, 2 t, J=6 Hz, 2 C—OH), 3.6–3.2 (m, 5H, O—CH($CH_2$—)$CH_2$—).

1D. Formula (4) where $R^2$ is Ethyl and $R^3$ is —$CH_2OC(O)CH_2CH_3$, varying the Catalyst Similarly, following the procedure of Example 1A above, but replacing trifluoromethane sulfonic acid by ammonium sulfate, the diester of Formula (4) was obtained in 72% yield. HPLC analysis typically indicated an N-9 to N-7 alkylation ratio between about 20:1 to 40:1 in this reaction.

Similarly, following the procedure of Example 1A above, but replacing trifluoromethane sulfonic acid by trimethylsilyl triflouromethanesulfonate, the diester of Formula (4) was obtained in 84% yield. HPLC analysis typically indicated an N-9 to N-7 alkylation ratio between about 20:1 to 30:1 in this reaction.

1E. Formula I where $R^1$ is Hydrogen

Similarly, following the procedures of Examples 1A, 1B, and 1C above, but substituting 2-oxa-1,4-butanediol diacetate for 2-propionoxymethoxy-3-propionoxypropyl propionate, the following compound of Formula I is prepared:

9-(2-hydroxyethoxy)methylguanine.

Example 2

Alternative Preparation of Compounds of Formula (I) where $R^1$ is —$CH_2OH$

2A. Formula (6) where $R^2$ is Ethyl, $R^3$ is —$CH_2OC(O)CH_2CH_3$, and $R^8$ is Methyl Diacetylguanine (3 g) was refluxed in a mixture of water (5 ml) and methanol (50 ml) for 4 hours. The solvents were then removed under reduced pressure, the residue washed with cold methanol, and dried under vacuum, to give N-acetylguanine, a compound of Formula (1a).

This product was mixed with hexamethyldisilazane (50 ml), and trifluoromethane sulfonic acid (0.1 ml), and refluxed for 16 hours. Excess reactant was removed under reduced pressure (35°–100° C., 0.1 mm), giving disilylated N-acetylguanine, a compound of Formula (2a).

The silylated product was then mixed with 2-propionoxymethoxy-3-propionoxypropyl propionate (4.5 g). The resulting mixture was heated at 120° C. for 7 hours, and cooled to 100° C. Methanol (5 ml) and toluene (5 ml) were then added, refluxed for 2 hours, then cooled to 0° C. for 16 hours. The product was filtered off, washed with toluene, and dried, to yield 9-(1,3-dipropionoxy- 2-propoxymethyl)-$N^2$-acetylguanine, a compound of Formula (6) as a yellow crystalline product.

The compound of Formula (6) was then hydrolysed to the compound of Formula I as described in Example 1C, to give pure 9-(1,3-dihydroxy-2-propoxymethyl)guanine.

2B. Formula I where $R^1$ is Hydrogen

Similarly, following the procedures of Example 2A above, but substituting 2-oxa-1,4-butanediol diacetate for 2-propionoxymethoxy-3-propionoxypropyl propionate, the following compound of Formula I is prepared:

9-(2-hydroxyethoxy)methylguanine.

Example 3

Preparation of Compounds of Formula (I) where $R^1$ is Hydrogen

3A. Formula (4) where $R^2$ is Ethyl and $R^3$ is Hydrogen

A mixture of 10 gms (66 mmoles) of guanine, 50 ml of hexamethyldisilazane, and 0.4 gms (3 mmmol) of ammonium sulfate was heated to 115°–118° C. for 18 hours. The ammonia gas was removed as it was formed. After 18 hours of heating, a solution was formed indicating the completion of silylation. To this solution was added 15 gms (85 mmol) of 2-oxa-1,4-butanediol diacetate and 0.1 ml of trimethylsilyl triftriflate. The mixture was heated to 130° C. for a period of 4.5 hours. The solution was cooled to 50° C. and 10 ml of water dissolved in 100 ml of acetone was added. The mixture was heated to reflux and a precipitate was formed immediately. The mixture was cooled and the solid was collected by filtration to yield 10.1 g (58% yield) of 9-(2-acetoxyethoxy)methylguanine, with a 13:1 ratio of N-9 to N-7 isomer. Characteristic analytical data are as follows: $^1$H NMR (DMSO-$d_6$) δ1.90 (3H, singlet, —OAc), 3.58 (2H, multiplet, —$OCH_2$—), 4.0 (2H, multiplet, —$CH_2OAc$), 5.25 (2H, singlet, —$NCH_2O$—), 6.5 (2H, br singlet, —$NH_2$), 7.75 (1H, singlet, —N=CH—N—).

Similarly, by following the procedures described above in Example 3A and substituting 2-oxa-1,4-butanediol diacetate with 2-oxa-1,4-butanediol dipropionate, 9.8 gm of 9-(2- propionoxyethoxy)methylguanine (53% yield) was obtained with a N-9/N-7 isomer ratio of 13.5:1. Characteristic analytical data are as follows: $^1$H NMR (DMSO-d$_6$) δ0.92 (3H, triplet, —CH$_3$), 2.08 (3H, singlet, —NHC=OCH$_3$), 2.13 (2H, triplet, —CH$_2$CH$_3$), 3.6 (2H, multiplet, —OCH$_2$—), 4.03 (2H, multiplet, —CH$_2$O—), 5.42 (2H, singlet, —NCH$_2$O—), 8.07 (1H, singlet, —N=CH—N—).

3B. Formula (6) where $R^2$ is Ethyl, $R^3$ is Hydrogen, and $R^8$ is Methyl 9-(2-Acetoxyethoxy)methylguanine (2 gms, 7.5 mmol) was dissolved in 15 ml of acetic anhydride. The mixture was heated to 120° C. and 0.1 gms (0.8 mmol) of 4-dimethylaminopyridine (DMAP) added. The reaction mixture was kept at 120° C. for 3 hours, then the mixture was cooled to 40° C. and 10 ml of toluene added. Hexane (20 ml) was added slowly to effect crystallization of the product. The solid was collected by filtration and washed with hexane, yielding 1.82 gms of 9-(2-acetoxyethoxy)methyl-N$^2$-acetylguanine (79%) with a N-9/N-7 isomer ratio of >200:1. Characteristic analytical data are as follows: $^1$H NMR (DMSO-d$_6$) δ1.85 (3H, singlet, —NHCOCH$_3$), 2.08 (3H, singlet, —O$_2$CCH$_3$), 3.6 (2H, multiplet, —OCH$_2$—), 3.95 (2H, multiplet, —CH$_2$O—), 5.4 (2H, singlet, —NCH$_2$O—), 8.06 (1H, singlet, —N=CH—N—).

By following the procedures described above in Example 3B, substituting 9-(2-acetoxyethoxy)methylguanine with 9-(2-propionoxyethoxy)methylguanine, 9-(2-propionoxyethoxy)methyl-N$^2$-acetylguanine was obtained with a N-9/N-7 isomer ratio of >99:1. Characteristic analytical data are as follows: $^1$H NMR (DMSO-d$_6$) δ0.92 (3H, triplet, —CH$_3$), 2.08 (3H, singlet, —NHC=OCH$_3$), 2.13 (2H, triplet, —CH$_2$CH$_3$), 3.6 (2H, multiplet, —OCH$_2$—), 4.03 (2H, multiplet, —CH$_2$O—), 5.42 (2H, singlet, —NCH$_2$O—), 8.07 (1H, singlet, —N=CH—N—).

3C. Preparation of Formula I Where $R^1$ is Hydrogen 9-(2-Acetoxyethoxy)methyl-N$^2$-acetylguanine (1.3 gm, 4.2 mmol) was dissolved in 10 ml of methanol and 10 ml of concentrated ammonium hydroxide, and the solution was heated at 50° C. for a period of 4 hours. The solvents were evaporated off, yielding a solid. The solid was recrystallized from methanol, yielding 0.85 gm of 9-(2-hydroxyethoxy)methylguanine (90% yield). Characteristic analytical data are as follows: $^1$H NMR(DMSO-d$_6$), δ3.16 (4H, singlet, —OCH$_2$CH$_2$O—), 4.6 (1H, br singlet, —OH), 5.26 (2H, singlet, —NCH$_2$—), 6.45 (2H, br singlet, —NH$_2$), 7.76 (1H, singlet, —N=CH—N—).

By following the procedures described above in Example 3C and substituting 9-(2-acetoxyethoxy)methyl-N$^2$-acetylguanine with 9-(2-propionoxyethoxy)methyl-N$^2$-acetylguanine, 0.82 gm of 9-(2-hydroxyethoxy)methylguanine (87% yield) was obtained.

Example 4

Alternative Preparation of Compounds of Formula (6)

4A. Formula (4) where $R^2$ is Ethyl and $R^3$ is —CH$_2$OC(O)CH$_2$CH$_3$

A mixture of guanine (20 g), hexamethyldisilazane (HMDS, 100 ml), and trifluoromethane sulfonic acid (0.48 ml) was heated to reflux (130°–135° C.) for 8 hours. The resulting mixture was cooled to 105° C., and excess HMDS removed by distillation (0.1 to 1 mm Hg). The mixture was then cooled to 100° C., and 3-propionyloxy-2-propionyloxymethoxypropyl propionate (54.2 g) added. The resulting mixture was heated to 120°–125° C. for 7 hours, and the low boiling material removed by distillation. The resulting reaction mixture, persilyl 9-(1,3-dipropionoxy-2-propoxymethyl)guanine as a solution, was cooled to 100° C. and used as such in the next reaction without further purification. The N-9 to N-7 alkylation ratio obtained in this reaction was about 34:1.

4B. Formula (6) where $R^2$ is Ethyl, $R^3$ is —CH$_2$OC(O)CH$_2$CH$_3$, and $R^8$ is Ethyl To the resulting reaction mixture of Example 1A at 105° C. was added a mixture of dimethylaminopyridine (1.32 g) and propionic anhydride (25.6 ml), and the mixture was stirred at 100° C. for 1.5 hour. A mixture of methanol (16 ml) and toluene (200 ml) was then added, and the mixture refluxed for 30 minutes. The resulting solution was slowly cooled to 0° C. over 2 hours, and maintained at 0° C. for 1 hour. The precipitate thus obtained was filtered off, washed with toluene (100 ml), and dried under reduced pressure (45° C., 60 mm) to afford 9-(1,3-propionoxy-2-propoxymethyl)-N$^2$-propionylguanine (39 g, 69.5% yield).

Example 5

Preparation of Compounds of Formula (3a) where $R^2$ is Ethyl

5A. Preparation of Formula (c)

A mixture of 1,3-dichloro-2-propanol (10 gm) and paraformaldehyde (3.02 gm) in dichloromethane (100 ml) was cooled to −5° C., and gaseous hydrogen chloride bubbled into the mixture over 25 minutes. The resultant mixture was kept at −8° C. for 14 hours. Sodium sulfate (2 gm) was then added, and the mixture stirred at room temperature for 2 hours. The solid was filtered off, and the filtrate washed with 20% aqueous sodium hydroxide (2×20 ml), and the aqueous phase removed. Solvent was removed from the organic phase under reduced pressure, giving 2-(chloromethoxy)-1,3-dichloropropane as a colorless liquid (13.21 gm, 96.1% yield).

5B. Preparation of Formula (3a) where $R^2$ is Ethyl

A mixture of sodium propionate (142.1 g) and 300 ml of toluene was heated to reflux, removing any water that azeotropes off. To the dry refluxing mixture 2-(chloromethoxy)-1,3-dichloropropane (75 g) was added slowly, followed by a solution of tetrabutylphosphonium chloride (12.5 g) in toluene. After refluxing for 12 hours, the mixture is cooled to 20°–25° C. and a solution of sodium carbonate (2.5 g) in 200 ml of water added. The mixture was stirred for 15 minutes, the aqueous layer separated, and the toluene layer washed with water. The combined aqueous extracts were washed with toluene, and the combined toluene extracts were filtered through silica-alumina. Toluene was removed from the filtrate under reduced pressure, giving 3-propionyloxy-2-propionyloxymethoxypropyl propionate (120 g).

What is claimed is:

1. A process for making a compound represented by the formula:

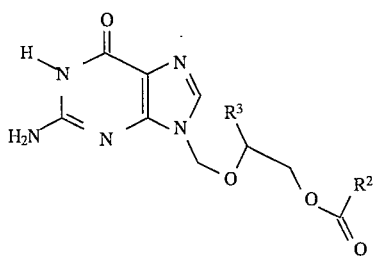

(4)

wherein:

R² is lower alkyl; and

R³ is hydrogen or —CH₂OC(O)R⁴;
in which R⁴ is lower alkyl;

said process comprising:

contacting a compound or mixture of compounds represented by the formula:

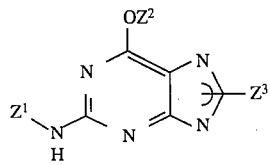

(2)

wherein:

Z¹ is hydrogen or R⁵R⁶R⁷Si;
Z² is hydrogen or R⁵R⁶R⁷Si;
Z³ is hydrogen or R⁵R⁶R⁷Si;
in which R⁵, R⁶, and R⁷ are independently lower alkyl; provided that at least one Z is R⁵R⁶R⁷Si; with a compound of the formula:

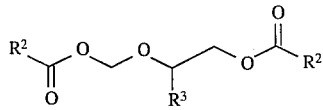

(3)

in the presence of about 0.01 to 0.1 molar equivalents of a selective alkylation catalyst selected from the group consisting of trifluoromethane sulfonic acid, trimethylsilyl trifluoromethanesulfonate, and bistrimethylsilyl sulfonate.

2. The process of claim 1, wherein said selective alkylation catalyst is trimethylsilyl trifluoromethanesulfonate.

3. The process of claim 2, wherein R⁵, R⁶, and R⁷ are all methyl.

4. The process of claim 3, in which both the compound of Formula (2) and the trimethylsilyl trifluoromethanesulfonate are generated concurrently by contacting guanine with hexamethyldisilazane in the presence of trifluoromethanesulfonic acid.

5. The process of claim 4, wherein the compound of Formula (2) is a compound of the formula:

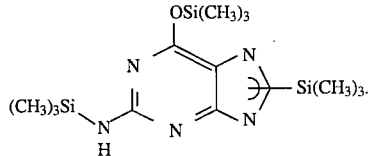

6. The process of claim 5 wherein R² is ethyl and R³ is —CH₂OC(O)R⁴, in which R⁴ is ethyl.

7. The process of claim 5, wherein R² is ethyl and R³ is hydrogen.

8. The process of claim 1, comprising the further steps of a) contacting the compound of Formula (4) with an acylating agent having an acyl radical of formula R⁸C(O)—, where R⁸ is lower alkyl or phenyl; optionally in the presence of a base, to give a compound represented by the formula:

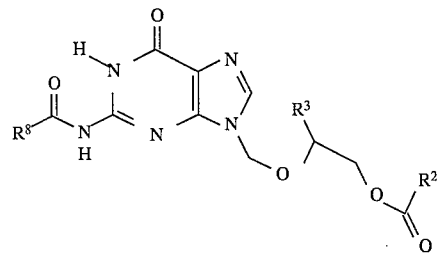

(6)

where R², R³, R⁸ are as defined above;

b) separating the compound represented by Formula (6); and c) hydrolyzing the separated compound of Formula (6) to give a compound of the Formula:

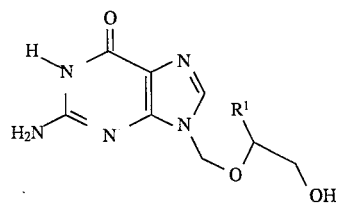

wherein:

R¹ is hydrogen or —CH₂OH.

9. The process of claim 8, in which the selective alkylation catalyst is trimethylsilyl trifluoromethanesulfonate and both the compound of Formula (2) and the trimethylsilyl trifluoromethanesulfonate are generated concurrently by contacting guanine with hexamethyldisilazane in the presence of trifluoromethanesulfonic acid.

10. The process of claim 9 wherein said acylating agent is propionic anhydride and said optional base is present and is 4-dimethylaminopyridine.

11. The process of claim 10, wherein the compound of Formula (6) is separated by crystallizing from an inert solvent.

12. The process of claim 11, wherein said inert solvent is isopropyl acetate, or toluene optionally mixed with hexane.

13. The process of claim 12, wherein said hydrolysis is carried out with ammonium hydroxide.

14. The process of claim 13, wherein R² is ethyl and R³ is hydrogen.

15. The process of claim 13, wherein R² is ethyl and R³ is —CH₂OC(O)R⁴, in which R⁴ is ethyl.

16. A process for making a compound represented by the formula:

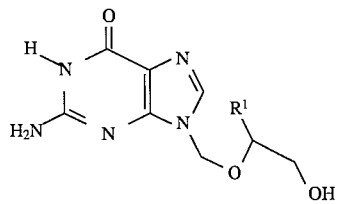

wherein:

R¹ is hydrogen or —CH₂OH;

said process comprising:

a) contacting a mixture of isomers represented by the formula:

in which $R^5$, $R^6$, and $R^7$ are independently lower alkyl and $R^8$ is lower alkyl or phenyl;

with a compound represented by the formula:

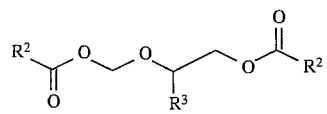

wherein:
$R^2$ is lower alkyl; and
$R^3$ is hydrogen or $-CH_2OC(O)R^4$;
in which $R^4$ is lower alkyl;
in the presence of about 0.01 to 0.1 molar equivalents of a selective alkylation catalyst selected from the group consisting of trifluoromethane sulfonic acid, trimethylsilyl trifluoromethanesulfonate, and bistrimethylsilyl sulfonate, to give a compound represented by the formula:

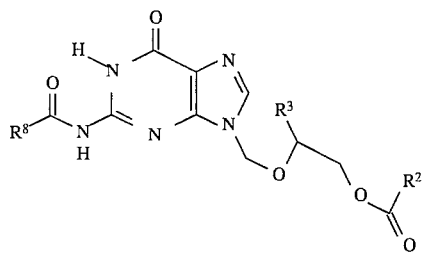

where $R^2$, $R^3$ and $R^8$ are as defined above;
b) separating the compound of Formula (6); and
c) hydrolyzing the separated compound of Formula (6).

17. The process of claim 16, wherein said selective alkylation catalyst is trimethylsilyl trifluoromethanesulfonate.

18. The process of claim 17, wherein $R^5$, $R^6$ and $R^7$ are all methyl and $R^2$ and $R^8$ are independently methyl or ethyl.

19. The process of claim 18, wherein the compound of Formula (6) is separated by crystallization from isopropyl acetate, or toluene optionally mixed with hexane.

20. The process of claim 19, wherein said hydrolysis is carried out with ammonium hydroxide.

21. The process of claim 20, wherein $R^2$ is ethyl and $R^3$ is $-CH_2OC(O)R^4$, in which $R^4$ is ethyl.

22. The process of claim 20, wherein $R^2$ is ethyl and $R^3$ is hydrogen.

23. A process for making a compound represented by the formula:

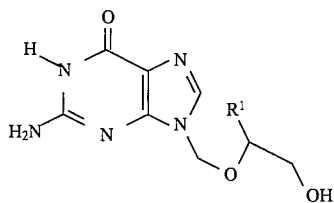

wherein:
$R^1$ is $-CH_2OH$; said process comprising:
a) contacting a mixture of isomers represented by the formula:

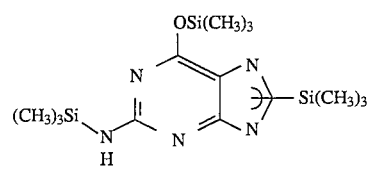

with a compound of the formula:

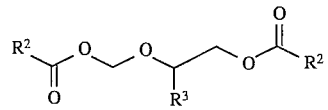

wherein:
$R^2$ is ethyl; and
$R^3$ is $-CH_2OC(O)C_2H_5$;
in the presence of trimethylsilyl trifluoromethanesulfonate, to obtain a compound of the formula:

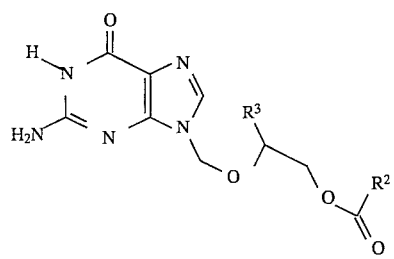

where $R^2$ and $R^3$ are as defined above:
b) contacting the compound of Formula (4) with propionic anhydride and dimethylaminopyridine, to give a compound represented by the formula:

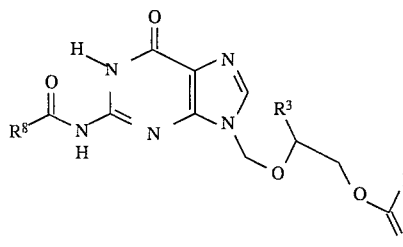

where $R^2$ is ethyl, $R^3$ is $-CH_2OC(O)C_2H_5$, and $R^8$ is ethyl;
c) crystallizing the compound represented by Formula (6) from toluene; and
d) hydrolyzing the crystallized compound of Formula (6) with ammonium hydroxide.

24. The process of claim 23, in which both the compound of Formula (2) and the trimethylsilyl trifluoromethanesulfonate are generated concurrently by contacting guanine with hexamethyldisilazane in the presence of trifluoromethanesulfonic acid.

* * * * *